United States Patent [19]

French et al.

[11] Patent Number: 5,399,739
[45] Date of Patent: Mar. 21, 1995

[54] METHOD OF MAKING SULFUR-CONTAINING ORGANOSILANES

[75] Inventors: J. Allen French, Wilmington; James E. Lee, Wilimington, both of N.C.

[73] Assignee: Wright Chemical Corporation, Riegelwood, N.C.

[21] Appl. No.: 228,728

[22] Filed: Apr. 18, 1994

[51] Int. Cl.$^6$ ................................................ C07F 7/08
[52] U.S. Cl. .................................................... 556/427
[58] Field of Search ........................................ 556/427

[56] References Cited

U.S. PATENT DOCUMENTS

| | | | |
|---|---|---|---|
| 3,842,111 | 10/1974 | Meyer-Simon et al. | 260/448.2 E |
| 3,849,471 | 11/1974 | Omietanski et al. | 260/448.2 E |
| 3,873,489 | 3/1975 | Thurn et al. | 556/427 X |
| 3,946,059 | 3/1976 | Janssen et al. | 260/448.2 N |
| 3,978,103 | 8/1976 | Meyer-Simon et al. | 556/427 |
| 3,997,356 | 12/1976 | Thurn et al. | 106/288 |
| 3,997,581 | 12/1976 | Pletka et al. | 260/448.2 E |
| 4,072,701 | 2/1978 | Pletka et al. | 260/448.8 R |
| 4,125,552 | 11/1978 | Speier | 260/448.8 R |
| 4,129,585 | 12/1978 | Buder et al. | 260/448.8 R |
| 4,269,963 | 5/1981 | Homan et al. | 528/17 |
| 4,384,132 | 5/1983 | Schwarz et al. | 556/427 |
| 4,408,064 | 10/1983 | Schwarz et al. | 556/427 |
| 4,507,490 | 3/1985 | Panster et al. | 556/427 |
| 5,110,969 | 5/1992 | Dittrich et al. | 556/427 |

OTHER PUBLICATIONS

*J. Org. Chem.*, vol. 43, No. 9, 1978, "Synthesis of Thiols and Polysulfides from alkyl Halides, Hydrogen Sulfide, Ammonia, and Sulfur", James E. Bittell and John L. Speier, pp. 1687–1689.

*Primary Examiner*—Paul F. Shaver
*Attorney, Agent, or Firm*—Bell, Seltzer, Park & Gibson

[57] ABSTRACT

A method for making sulfur-containing organosilanes of Formula (I):

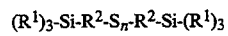

wherein each $R^1$ is independently selected from the group consisting of a $C_1$–$C_4$ alkyl, a $C_1$–$C_4$ alkoxy, a $C_5$–$C_8$ cycloalkyl, a $C_5$–$C_8$ cycloalkoxy, a phenyl group, or a phenoxy group, a benzyl group or a benzyloxy group; $R^2$ is a $C_1$–$C_4$ alkyl; and n is a number from 3–4. The method comprises (a) dissolving an alkali metal in a $C_1$–$C_4$ alcohol to provide an alkali metal alcoholate, (b) reacting hydrogen sulfide with the alkali metal alcoholate of step (a) to provide an alkali metal hydrosulfide, (c) reacting an alkali metal with the alkali metal hydrosulfide of step (b) to provide an alkali metal sulfide, (d) reacting sulfur with the alkali metal sulfide of step (c) to provide an alkali metal polysulfide, and (e) reacting a compound of Formula (II): $X$-$R^2$-$Si(R^1)_3$, wherein $R^1$ and $R^2$ are as defined above, and X is a halogen selected from the group consisting of chlorine or bromine, with the alkali polysulfide of step (d) to provide the sulfur-containing organosilane compound of Formula I.

20 Claims, No Drawings

METHOD OF MAKING SULFUR-CONTAINING ORGANOSILANES

FIELD OF THE INVENTION

The present invention relates to a method of making silane compounds which are useful in the tire manufacturing industry, and particularly to a method of making sulfur-containing organosilicon compounds.

BACKGROUND OF THE INVENTION

Organosilane compounds are commonly used in the tire manufacturing and rubber vulcanizates industries. Typically, these compounds act as bonding agents in vulcanizable rubbers containing reinforcing filler material such as silica and carbon black.

A number of different methods have been proposed for producing such compounds. For example, U.S. Pat. No. 3,842,111 to Meyer-Simon et al. describes a process for the production of bis(alkoxysilylalkyl)oligosulfides from the corresponding alkoxysilylhalides and alkali metal oligosulfides, preferably in alcoholic solution.

U.S. Pat. No. 4,072,701 to Pletka proposes a method of making bis-(alkoxysilylalkyl)oligosulfides by the reaction of alkoxysilylalkylhalides, metal or ammonium hydrogen sulfides and sulfur. This reaction, however, produces quantities of a toxic by-product, namely hydrogen sulfide, and is therefore not deemed industrially practical.

U.S. Pat. No. 4,129,585 to Buder et al. describes a method of making bis-(alkoxysilylalkyl)oligosulfides by the reaction of an alkali metal alcoholate, with an alkoxysilylorganylhalide, metal or ammonium hydrogen sulfide, and sulfur in the presence of an organic solvent.

U.S. Pat. No. 4,507,490 to Panster et al. describes a method of making sulfur-containing organosilicon compounds by dissolving a metal hydrogen sulfide in an organic solvent, treating with an alkali metal and optionally sulfur, and directly subsequently further reacting with a haloalkylsilane.

There remains, however, a need in the art for an industrially practical, one-kettle reaction method of producing sulfur-containing organosilane compounds which results in high yield without the production of toxic by-products.

SUMMARY OF THE INVENTION

It is therefore an object of the present invention to provide a method of producing sulfur-containing organosilane compounds which results in high yield while avoiding the production of toxic by-products.

Accordingly, the present invention comprises a method of making a sulfur-containing organosilane compound having the formula:

$$(R^1)_3\text{-Si-}R^2\text{-S}_n\text{-}R^2\text{-Si-}(R^1)_3 \qquad (I)$$

wherein each $R^1$ is independently selected from the group consisting of a $C_1$–$C_4$ alkyl, a $C_1$–$C_4$ alkoxy, a $C_5$–$C_8$ cycloalkyl, a $C_5$–$C_8$ cycloalkoxy, a phenyl group or a phenoxy group, a benzyl group or a benzyloxy group; $R^2$ is a $C_1$–$C_4$ alkyl; and n is a number from 3–4. The method comprises the steps of: (a) dissolving an alkali metal in a $C_1$–$C_4$ alcohol to provide an alkali metal alcoholate; (b) reacting hydrogen sulfide with the alkali metal alcoholate of step (a) to provide an alkali metal hydrosulfide; (c) reacting an alkali metal with the alkali metal hydrosulfide of step (b) to provide an alkali metal sulfide; (d) reacting sulfur with the alkali metal sulfide of step (c) to provide an alkali metal polysulfide; and (e) reacting a compound of Formula (II): $X\text{-}R^2\text{-Si}(R^1)_3$, wherein $R^1$ and $R^2$ are as defined above, and X is a halogen selected from the group consisting of chlorine or bromine, with the alkali metal polysulfide of step (d).

The foregoing and other objects, advantages, and features of the present invention are explained in detail in the specification set forth below.

DETAILED DESCRIPTION OF THE INVENTION

As used herein, the terms "$C_1$–$C_4$ alkyl" refers to linear or branched alkyl groups having 1 to 4 carbon atoms therein. Term "$C_1$–$C_4$ alkoxy" refers to linear or branched alkoxy groups having 1 to 4 carbon atoms therein. The term "organosilane" refers to a sulfur-containing organosilane of the Formula (I).

The present invention comprises a method of providing an organosilane of the Formula:

$$(R^1)_3\text{-Si-}R^2\text{-S}_n\text{-}R^2\text{-Si-}(R^1)_3 \qquad (I)$$

wherein each $R^1$ is independently selected from the group consisting of a $C_1$–$C_4$ alkyl, a $C_1$–$C_4$ alkoxy, a $C_5$–$C_8$ cycloalkyl, a $C_5$–$C_8$ cycloalkoxy, a phenyl group or a phenoxy group, a benzyl group or a benzyloxy group; $R^2$ is a $C_1$–$C_4$ alkyl; and n is a number from 3–4. Preferably, $R^1$ is a $C_1$–$C_4$ alkoxy. More preferably, $R^1$ is ethoxy. $R^2$ is preferably a propyl group. Also preferably n is 4. In one particularly preferred embodiment, $R^1$ is ethoxy, $R^2$ is a propyl group and n is 4. An example of a preferred compound of Formula I is bis-(3-triethoxysilylpropyl) tetrasulfide.

As summarized above, the method comprises (a) dissolving an alkali metal in a $C_1$–$C_4$ alcohol to provide an alkali metal alcoholate; (b) reacting hydrogen sulfide with the alkali metal alcoholate of step (a) to provide an alkali metal hydrosulfide; (c) reacting an alkali metal with the alkali metal hydrosulfide of step (b) to provide an alkali metal sulfide; (d) reacting sulfur with the alkali metal sulfide of step (c) to provide an alkali metal polysulfide; and (e) reacting a compound of Formula (II): $X\text{-}R^2\text{-Si}(R^1)_3$, wherein $R^1$ and $R^2$ are as defined above, and X is a halogen selected from the group consisting of chlorine or bromine, with the alkali metal polysulfide of step (d) to provide the sulfur-containing organosilane compound of Formula I.

Preferably, the method is carried out as a one-kettle reaction, wherein the entire method is conducted in a single reaction vessel. The method may be conducted at ambient temperature and pressure conditions. The method may be carried out in a polar organic solvent, such as an alcohol. In one preferred embodiment, the polar organic solvent is the $C_1$–$C_4$ alcohol of step (a). It is particularly preferred to exclude water and air from the reaction vessel to avoid the preparation of side-products. Such conditions may be accomplished by conducting the reaction under a blanket of an inert gas such as nitrogen.

Referring to the first step of the reaction, step (a), the alkali metal may be dissolved in the $C_1$–$C_4$ alcohol according to any suitable method. Preferably, the reaction vessel is charged with alcohol and then the alkali metal is added and mixed therewith until the alkali metal is dissolved and reacted therein. The alcohol may be any $C_1$–$C_4$ alcohol in which the chosen alkali metal will dissolve. Typically, the alcohol is selected from the group consisting of methanol, ethanol, and isopropanol. The alkali metal is selected from the group consisting of sodium and potassium. In a particularly preferred embodiment, the alcohol is ethanol and the alkali metal is sodium.

Typically, the ratio of alcohol to alkali metal is sufficient to convert substantially all of the alkali metal to the alkali metal alcoholate (sometimes referred to as metal alcoholate). Preferably, about 0.5 to about 4 moles of the alkali metal is dissolved in about 7 to about 56 moles of the alcohol.

The second step of the method, step (b) comprises reacting hydrogen sulfide with the metal alcoholate provided by the first reaction step according to any suitable means. As the reaction is typically and preferably carried out as a one-kettle reaction, preferably the hydrogen sulfide is sparged into the metal alcoholate. Typically, the hydrogen sulfide is sparged into the metal alcoholate at a rate which is sufficient to allow the hydrogen sulfide to react with the metal alcoholate without producing an excess of non-reacted hydrogen sulfide gas in the reaction vessel. The optimum rate of addition will depend upon the batch size. Typically, the hydrogen sulfide is sparged into the reactor over a period of about 2 to about 4 hours. The quantity of hydrogen sulfide reacted with the metal alcoholate should be sufficient to convert substantially all of the metal alcoholate to the alkali metal hydrosulfide (also referred to as metal hydrosulfide). Preferably, about 0.5 to about 4 moles of hydrogen sulfide is reacted with the metal alcoholate.

The third step of the reaction (c) comprises reacting an alkali metal with the alkali metal hydrosulfide provided by the preceding reaction step. The alkali metal may be, selected from the group consisting of sodium and potassium, but should be the same alkali metal used in the preceding step (a). The alkali metal may be reacted with the metal hydrosulfide according to any suitable means. Preferably, the alkali metal is added to the reaction vessel containing the metal hydrosulfide and mixed therewith until development of hydrogen ceases. Typically, about 0.5 to about 4 moles of alkali metal is added.

The fourth step of the method, step (d), comprises reacting additional sulfur with the alkali metal sulfide provided by the preceding step (c) to provide an alkali metal polysulfide, and can be carried out according to any suitable means known to those skilled in the art. Preferably, the sulfur is elemental sulfur provided in finely divided form. An exemplary form of sulfur is commercial sulfur powder, obtainable from Aldrich Chemical Corp., Milwaukee, Wis. Preferably, sufficient quantities of sulfur are added to convert substantially all of the alkali metal sulfide to a tri- or tetrasulfide. More preferably, the quantity of sulfur added is sufficient to convert substantially all of the alkali metal sulfide to an alkali metal tetrasulfide. Typically, about 1.5 to about 12 moles of sulfur are added and reacted with the alkali metal sulfide.

The final step of the reaction, step (e), comprises reacting the thus produced alkali metal polysulfide with a compound of Formula II:

X-R$^2$-Si(R$^1$)$_3$ wherein R$^1$ and R$^2$ are defined as above for compounds of Formula (I), and X is a halogen selected from the group consisting of chlorine or bromine. Preferably, R$^1$ is a C$_1$–C$_4$ alkoxy. More preferably, R$^1$ is or ethoxy. R$^2$ is preferably a propyl group. X is preferably, chlorine.

Exemplary compounds of Formula (II) include but are not limited to: 3-chloropropyltriethoxysilane, 3-bromopropyltriethoxysilane, chloromethyltrimethoxysilane, 2-chloroethyldiethoxyethylsilane, 2-bromoethyltriisopropoxysilane, 2-chloroethyltriethoxysilane, 3-chloropropyltrimethoxysilane, 3-chloropropyldiethoxymethylsilane, 3-chloropropylcyclohexoxydimethylsilane, 4-bromobutyltriethyoxysilane, chlorobutyltrimethoxysilane, 3-bromo-isobutyltriethoxysilane, 3-chloropropyl-dimethoxy-p-ethylphenylsilane, 3-chloropropylethoxymethylethylsilane, 3-bromopropyldimethoxycyclopentoxysilane; 2-chloro-2'-methylethyldiethoxycycloheptoxysilane, 3-bromo-2'-methylpropyldimethoxycyclooctylsilane, 3-chloropropyl-diethoxy-2'-methoxyethoxysilane, 3-chloroethyldimethylcyclooctylsilane, 3-chloropropyldibutoxymethylsilane, 3-bromopropylphenyloxydimethoxysilane, 3-chloropropyldi-isobutoxy-2'-methylphenylsilane, 3-chloro-3'-methylpropyldimethoxybenzyloxysilane, and 3-chloropropyltributoxysilane. In one preferred embodiment, the compound of Formula (II) is 3-chloropropyltriethoxysilane, obtainable from Huls America Inc., Piscataway, N.J.

Typically, the amount of the compound of Formula (II) reacted with the alkali metal polysulfide is sufficient to provide a high yield of the compounds of Formula (I). Preferably, about 1 to about 8 moles of the compound of Formula (II) are added and reacted with the alkali metal polysulfide.

The foregoing method produces the sulfur-containing organosilanes and a salt by-product, which can easily be separated according to conventional means. Similarly, in the embodiment wherein the method is carried out in a polar organic solvent, the sulfur-containing organosilanes can be recovered according to conventional means.

Exemplary compounds of Formula (I) provided by the foregoing method include but are not limited to:

Preferred organosilanes of Formula (I) which may be produced by the method of the present invention include: bis-(3-trimethoxysilylpropyl) trisulfide, bis-(3-triethoxysilylpropyl) tetrasulfide, bis-(3-trimethoxysilylpropyl) tetrasulfide, bis-(2-triethoxy-silylethyl) tetrasulfide, bis-(3-triethoxysilylpropyl) trisulfide, bis-(3-tricyclooctoxysilylpropyl) tetrasulfide, bis-tri-(3-isobutoxysilylpropyl) tetrasulfide, bis-(tris-t-butoxysilylmethyl) trisulfide, bis-(2-methoxydiethoxysilylethyl) tetrasulfide, bis-(3-tricyclohexoxysilylpropyl) tetrasulfide, bis-(3-tricyclopentoxysilylpropyl) trisulfide, bis-(dimethoxyphenoxysilylmethyl) tetrasulfide, bis-(3-dimethoxymethyl silylpropyl) trisulfide, bis-(3-dimethoxymethyl silylpropyl) tetrasulfide, bis-(3-dimethoxyethyl silylpropyl) trisulfide, bis-(3-dimethoxyethyl silylpropyl) tetrasulfide, bis-(3-diethoxymethyl silylpropyl) trisulfide, bis-(3-diethoxymethyl silylpropyl) tetrasulfide, bis-(3-diethoxyethyl silylpropyl) trisulfide, bis-(3-diethoxyethyl silylpropyl) tetrasulfide, bis-(3-methoxydimethyl silylpropyl) trisulfide, bis-(3-methoxydimethyl silylpropyl) tetrasulfide, bis-(3-ethoxydimethyl silylpropyl) trisulfide, bis-(3-ethoxydimethyl silylpropyl) tetrasulfide, bis-(3-diethylethoxysilylpropyl) tetrasulfide, bis-(3-diisopropoxymethylsilylpropyl) trisulfide, bis-(3-diisopropoxymethylsilylpropyl) tetrasulfide, bis-(4-diethoxyethylsilylbutyl) trisulfide, bis-(5-phenyldimethoxysilylpentyl) tetrasulfide, bis-(2-dimethoxyphenylsilylethyl) trisulfide, bis-(3-methylbutylethoxysilylpropyl) tetrasulfide, bis-(2-ethyldiethoxysilyisopropyl) tetrasulfide. A particularly preferred compound of Formula (I) which can be produced according to the foregoing method is bis-(3-triethoxysilylpropyl) tetrasulfide.

The foregoing method produces the alkali metal polysulfide in the anhydrous form, and reacts in the anhydrous alkali metal polysulfide with the compound of Formula II to provide a higher yield than can be attained using conventional methods. The anhydrous form of the alkali metal polysulfide eliminates the side reaction which occur between trace amounts of water and the compounds of Formula II. This side reaction ultimately results in lowers yields of the compound of Formula I. By producing the alkali metal polysulfide in the anhydrous form, the method of the present invention eliminates this side reaction, and thereby produces a higher yield of the compounds of Formula I.

The following example is provided to illustrate the present invention, and should not be construed as limiting thereof. In this example, g means grams, mg means milligrams, l means liters, ml means milliliters, M means Molar, mol means mols, and min. means minutes.

EXAMPLE 1

A 22-liter reaction vessel, equipped with an agitator, is charged with 7,590 g of anhydrous ethyl alcohol. Thereafter, 70 g of sodium metal is added over an eight hour period, and the mixture is agitated until the sodium dissolves and the development of hydrogen gas ceases. The concentration of sodium ethoxide is measured by titration and determined to be 10.2%. Thereafter, 405 g of gaseous hydrogen sulfide is sparged into the vessel containing sodium ethoxide, over the course of 2 hours and 13 minutes, and the mixture is agitated, to produce sodium hydrosulfide. Thereafter, 255 g of sodium metal is added to the sodium hydrosulfide solution over 6 hours and 10 minutes, and the solution is agitated until the development of hydrogen gas ceases. Thereafter, 1,065 g of elemental sulfur is added over 20 minutes, and allowed to react under heat and agitation at 60° C. for 1 hour. Thereafter the solution was cooled overnight to ambient temperature, to produce sodium tetrasulfide in solution. 3-Chloropropyl triethoxysilane (5,548 g) is then added over one hour and 20 minutes, and allowed to react. The vessel is then heated to reflux (80.3° C.) for 2 hours and cooled slowly to room temperature. The reaction produced 41.4% of bis-(3-triethoxysilylpropyl) tetrasulfide. The product is separated from the sodium chloride by-product and ethanol solvent, and subsequently analyzed using elemental analysis. Analysis: theory C: 40.11, H: 7.84, S: 23.79, Si: 10.42; found C: 40.37, H: 7.74, S: 22.89, Si: 10.35. The structure is also confirmed using Infrared spectrometry.

The foregoing is illustrative of the present invention and is not to be construed as limiting thereof. The invention is defined by the following claims, with equivalents of the claims to be included therein.

That which is claimed is:

1. A method of making a sulfur-containing organosilane compound of the Formula (I): $(R^1)_3$-Si-$R^2$-$S_n$-$R^2$-Si-$(R^1)_3$, wherein: each $R^1$ is independently selected from the group consisting of a $C_1$-$C_4$ alkyl, a $C_1$-$C_4$ alkoxy, a $C_5$-$C_8$ cycloalkyl, a $C_5$-$C_8$ cycloalkoxy, a phenyl group, or a phenoxy group, a benzyl group or a benzyloxy group; $R^2$ is a $C_1$-$C_4$ alkyl; and n is a number from 3–4, said method comprising the steps of:
   (a) dissolving an alkali metal in a $C_1$-$C_4$ alcohol to provide an alkali metal alcoholate;
   (b) reacting hydrogen sulfide with the alkali metal alcoholate of step (a) to provide an alkali metal hydrosulfide;
   (c) reacting an alkali metal with the alkali metal hydrosulfide of step (b) to provide an alkali metal sulfide;
   (d) reacting sulfur with the alkali metal sulfide of step (c) to provide an alkali metal polysulfide; and
   (e) reacting a compound of Formula (II): X-$R^2$-Si$(R^1)_3$, wherein $R^1$ and $R^2$ are as defined above, and X is a halogen selected from the group consisting of chlorine or bromine with the alkali metal polysulfide of step (d) to provide the sulfur-containing organosilane compound of Formula I.

2. The method according to claim 1, wherein $R^1$ is a $C_1$-$C_4$ alkoxy.

3. The method according to claim 1, wherein $R^2$ is a propyl group.

4. The method according to claim 1, wherein $R^1$ is an ethoxy group.

5. The method according to claim 1, wherein n is 4.

6. The method according to claim 1, wherein the alkali metal is sodium.

7. The method according to claim 1, wherein the $C_1$-$C_4$ alcohol is selected from the group consisting of methanol, ethanol and isopropanol.

8. The method according to claim 1, wherein the $C_1$-$C_4$ alcohol is ethanol.

9. The method according to claim 1, wherein X is chlorine.

10. The method according to claim 1, wherein the alkali metal is sodium and the $C_1$-$C_4$ alcohol is ethanol.

11. The method according to claim 1, wherein the method is carried out in a polar organic solvent.

12. The method according to claim 11, wherein the polar organic solvent is ethanol.

13. A method of making a sulfur-containing organosilane compound of the Formula (I): $(R^1)_3$-Si-$R^2$-$S_n$-$R^2$-Si-$(R^1)_3$, wherein: $R^1$ is selected from the group consisting of a $C_1$-$C_4$ alkyl and $C_1$-$C_4$ alkoxy; $R^2$ is a propyl group; and n is 4, said method comprising the steps of:
   (a) dissolving an alkali metal in a $C_1$-$C_4$ alcohol to provide an alkali metal alcoholate;
   (b) reacting hydrogen sulfide with the alkali metal alcoholate of step (a) to provide an alkali metal hydrosulfide;
   (c) reacting an alkali metal with the alkali metal hydrosulfide of step (b) to provide an alkali metal sulfide;
   (d) reacting sulfur with the alkali metal sulfide of step (c) to provide an alkali metal polysulfide; and
   (e) reacting a compound of the Formula (II): X-$R^2$-Si$(R^1)_3$, wherein $R^1$ and $R^2$ are as defined above, and X is a halogen selected from the group consisting of chlorine or bromine with the alkali metal polysulfide of step (d) to provide the sulfur-containing organosilane compound of Formula I.

14. The method according to claim 13, wherein $R^1$ is an ethoxy group.

15. The method according to claim 13, wherein the alkali metal is sodium.

16. The method according to claim 13, wherein the $C_1$-$C_4$ alcohol is selected from the group consisting of methanol, ethanol and isopropanol.

17. The method according to claim 13, wherein the $C_1$-$C_4$ alcohol is ethanol.

18. The method according to claim 13, wherein X is chlorine.

19. The method according to claim 13, wherein the alkali metal is sodium and the $C_1$-$C_4$ alcohol is ethanol.

20. The method according to claim 13, wherein the method is carried out ethanol.

* * * * *

UNITED STATES PATENT AND TRADEMARK OFFICE
CERTIFICATE OF CORRECTION

PATENT NO. : 5,399,739

DATED : March 21, 1995

INVENTOR(S) : J. Allen French and James E. Lee

It is certified that error appears in the above-identified patent and that said Letters Patent is hereby corrected as shown below:

Column 5, line 28, please correct " 70 " to read -- 270 --.

Signed and Sealed this

Twenty-seventh Day of February, 1996

Attest:

BRUCE LEHMAN

Attesting Officer     Commissioner of Patents and Trademarks